(12) United States Patent
Kamada et al.

(10) Patent No.: US 11,041,823 B2
(45) Date of Patent: Jun. 22, 2021

(54) GAS SENSOR

(71) Applicant: NGK SPARK PLUG CO., LTD., Nagoya (JP)

(72) Inventors: Kentaro Kamada, Komaki (JP); Hitoshi Furuta, Tajimi (JP); Masaki Nakagawa, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 365 days.

(21) Appl. No.: 16/040,205

(22) Filed: Jul. 19, 2018

(65) Prior Publication Data
US 2019/0025245 A1    Jan. 24, 2019

(30) Foreign Application Priority Data

Jul. 20, 2017 (JP) .............................. JP2017-140713
Feb. 22, 2018 (JP) .............................. JP2018-029411

(51) Int. Cl.
*G01N 27/407* (2006.01)
*G01N 33/00* (2006.01)
*G01N 27/406* (2006.01)
*G01N 27/409* (2006.01)

(52) U.S. Cl.
CPC ....... *G01N 27/4078* (2013.01); *G01N 27/409* (2013.01); *G01N 27/4067* (2013.01); *G01N 33/0037* (2013.01)

(58) Field of Classification Search
CPC .......... G01N 27/4078; G01N 27/4067; G01N 27/4071; G01N 27/409; G01N 33/0037; G01N 27/41
See application file for complete search history.

(56) References Cited

U.S. PATENT DOCUMENTS

| 6,287,439 | B1 | 9/2001 | Kato et al. | |
| 2006/0162422 | A1* | 7/2006 | Geier | G01N 27/407 73/23.31 |
| 2007/0235332 | A1* | 10/2007 | Sugiyama | G01N 27/4075 204/424 |
| 2009/0314056 | A1* | 12/2009 | McCauley | G01N 27/4078 73/23.31 |
| 2011/0254428 | A1* | 10/2011 | Kyuno | H01T 13/36 313/135 |

(Continued)

FOREIGN PATENT DOCUMENTS

| JP | 10-318979 A | 12/1998 |
| JP | 2004226332 A | * 8/2004 |

*Primary Examiner* — Maris R Kessel
(74) *Attorney, Agent, or Firm* — Sughrue Mion, PLLC (57) ABSTRACT

A gas sensor (1) including: a sensor element (10) which includes a detection portion (11) and a heater (50); a metal shell (138); and a filled member (153) filled with a filling material between the metal shell and the sensor element, wherein a position at which change in a temperature of the sensor element is smallest when a disturbance is applied is a temperature reference position M, the filled member is positioned rearward of the temperature reference position, an overall axial length LT of the sensor element is not greater than 50 mm, an axial length LE from a rear end of the filled member to a rear end of the sensor element is not smaller than 13.5 mm, and an axial length LA from the temperature reference position to a front end of the filled member is greater than 5.0 mm and not greater than 11.5 mm.

4 Claims, 6 Drawing Sheets

(56) References Cited

U.S. PATENT DOCUMENTS

| | | | |
|---|---|---|---|
| 2015/0268187 A1* | 9/2015 | Adachi | G01N 27/4078 204/424 |
| 2015/0330939 A1* | 11/2015 | Tahira | G01N 27/4078 29/25.03 |
| 2018/0217088 A1* | 8/2018 | Tahira | G01N 27/4078 |

* cited by examiner

GAS SENSOR

BACKGROUND OF THE INVENTION

1. Field of the Invention

The present invention relates to a gas sensor including a sensor element for measuring a specific gas component.

2. Description of the Related Art

A gas sensor including a plate-shaped sensor element using a solid electrolyte is known as a gas sensor for detecting the concentration of a specific gas component such as oxygen or NOx in exhaust gas or an intake charge mixture from/in an automobile, etc. (Patent Document 1). A detection portion for detecting the specific gas component, and a heater for heating the detection portion to an activation temperature, are provided on the front side of the sensor element.

The gas sensor includes a metal shell surrounding the periphery of the sensor element, a gap between the metal shell and the sensor element is sealed by talc, and heating by the heater is controlled such that the temperature of the sensor element at a predetermined position on the front side becomes constant.

[Patent Document 1] Japanese Patent Application Laid-Open (kokai) No. H10-318979

3. Problems to be Solved by the Invention

As the length of the sensor element is shortened in order to reduce the size of the gas sensor, the talc filler is arranged closer to the front side of the sensor element, and heat of the sensor element more easily escapes from the talc into the metal shell. Meanwhile, the position at which the talc is assembled relative to the sensor element is not constant, but varies within a range of manufacturing error. Thus, the degree of heat conduction from the sensor element also varies depending on the configuration of the individual gas sensors. As a result, a problem arises in that the power supplied to the heater to heat the sensor element increases and the time period required for heating is elongated. Consequently, it becomes difficult to promptly activate the gas sensor.

In particular, low voltage operation is required of electronic components incorporated into an automobile and the like, and accordingly, an operating voltage for the heater is also set to a minimal value required for heating. Thus, if there is a manufacturing variation among gas sensors, it becomes difficult to perform the heating operation at a low voltage.

SUMMARY OF THE INVENTION

It is therefore an object of the present invention to provide a gas sensor which enables a reduction in the size of the gas sensor, and in which variation in heat conduction from a sensor element due to a manufacturing variation among gas sensors is reduced so that an increase in power that is to be supplied to the heater is suppressed.

In order to solve the above-described problems, the present invention provides (1) a gas sensor which comprises a sensor element which is plate-shaped so as to extend in a direction of an axial line and which includes a detection portion arranged at a front end side of the sensor element having at least one cell comprising a solid electrolyte and a pair of electrodes formed on the solid electrolyte and which includes a heater configured to heat the detection portion; a metal shell which has a through hole penetrating therethrough in the direction of the axial line and which surrounds a periphery of the sensor element; and a filled member filled with a filling material between an inner side surface of the metal shell and an outer surface of the sensor element so as to seal a gap between the metal shell and the sensor element, the filled member having a front end and a read end, the sensor element being configured to be heated to a set temperature by the heater. A position at which a resulting change in temperature of the sensor element is smallest when a disturbance is applied thereto is defined as a temperature reference position, the filled member is positioned rearward of the temperature reference position of the sensor element, an overall length LT in the direction of the axial line of the sensor element is not greater than 50 mm, a length LE in the direction of the axial line from a rear end of the filled member to the rear end of the sensor element is not smaller than 13.5 mm, and a length LA in the direction of the axial line from the temperature reference position to a front end of the filled member is greater than 5.0 mm and not greater than 11.5 mm.

According to the above gas sensor (1), by setting LT so as not to be greater than 50 mm, the length of the sensor element is shortened so that the size of the gas sensor is reduced. Further, by setting LE being to not smaller than 13.5 mm, the dimension of, for example, an electrode pad 10a formed on the rear side of the sensor element and the interval between the electrode pads 10a are ensured, whereby the reliability of electrical connection with a metal terminal and the like can be improved.

Furthermore, by setting LA within a range larger than 5.0 mm and not larger than 11.5 mm, a variation in heat conduction from the sensor element to the filled member is small even if there is a variation in LA at the time of gas sensor assembly, whereby an increase in power that is to be supplied to the heater can be suppressed and the sensor element can be operated at a low voltage.

In a preferred embodiment (2) of the gas sensor (1), LA is not smaller than 6.7 mm and not larger than 10.7 mm.

According to the above gas sensor (2), when there is a variation in LA at the time of gas sensor assembly, the variation in heat conduction from the sensor element to the filled member becomes even smaller. Accordingly, an increase in power that is to be supplied to the heater can be further suppressed.

In another preferred embodiment (3) of the gas sensor (1) or (2) above, the temperature reference position is a position of a region in which electrodes constituting a detection cell configured to detect a specific gas component in a measurement target gas overlap.

According to the above gas sensor (3), the temperature of the detection cell can be accurately and easily measured even at the temperature reference position based on the fact that the internal impedance of the detection cell is proportional to its temperature.

In yet another preferred embodiment (4) of the gas sensor of any of (1) to (3) above, the filled member is filled with talc.

Talc is easily filled between the inner side surface of the metal shell and the outer surface of the sensor element, and thus, the gap therebetween can be assuredly sealed.

In yet another preferred embodiment (5) of the gas sensor of any of (1) to (4) above, the filled member includes a first filled member and a second filled member arranged on a rear side of the first filled member, a length in the direction of the axial line from a rear end of the second filled member positioned so as to be farthest from the sensor element, to the rear end of the sensor element, is defined as LE, and a length in the direction of the axial line from the temperature reference position to a front end of the first filled member positioned so as to be closest to a front end of the sensor element is defined as LA.

According to the above gas sensor (5), in the case where the plurality of filled members are arranged in the direction of the axial line, LA is defined with respect to the first filled member at which heat conduction from the sensor element is the most conspicuous. Accordingly, even in the case where a plurality of filled members are present, an increase in power that is to be supplied to the heater can be suppressed, and the sensor element can be operated at a low voltage.

Furthermore, LE is defined with respect to the second filled member which is farthest from the sensor element. Accordingly, even in the case where a plurality of filled members is present, reliability of electrical connection with the metal terminal and the like can be improved.

Effects of the Invention

The present invention enables reduction in the size of a gas sensor, and in which variation in heat conduction from a sensor element due to a manufacturing variation among gas sensors is reduced so that an increase in power that is to be supplied to the heater is suppressed.

DESCRIPTION OF REFERENCE NUMERALS

Reference numerals used to identify various features in the drawings include the following.
1: gas sensor
10: sensor element
10e: rear end of sensor element
11: detection portion
15 to 17: cell
15a, 15b, 16a, 16b, 17a, 17b: pair of electrodes
15c to 17c: solid electrolyte
50: heater
138: metal shell
154: through hole of metal shell
153, 253, 255: filled member
253: first filled member
255: second filled member
153e, 255e: rear end of filled member
153f, 253f: front end of filled member
M: temperature reference position
O: axial line

DETAILED DESCRIPTION OF THE PREFERRED EMBODIMENTS

Hereinafter, an embodiment of the present invention will be described in greater detail with reference to the drawings. However, the present invention should be construed as being limited thereto.

Figure 1:
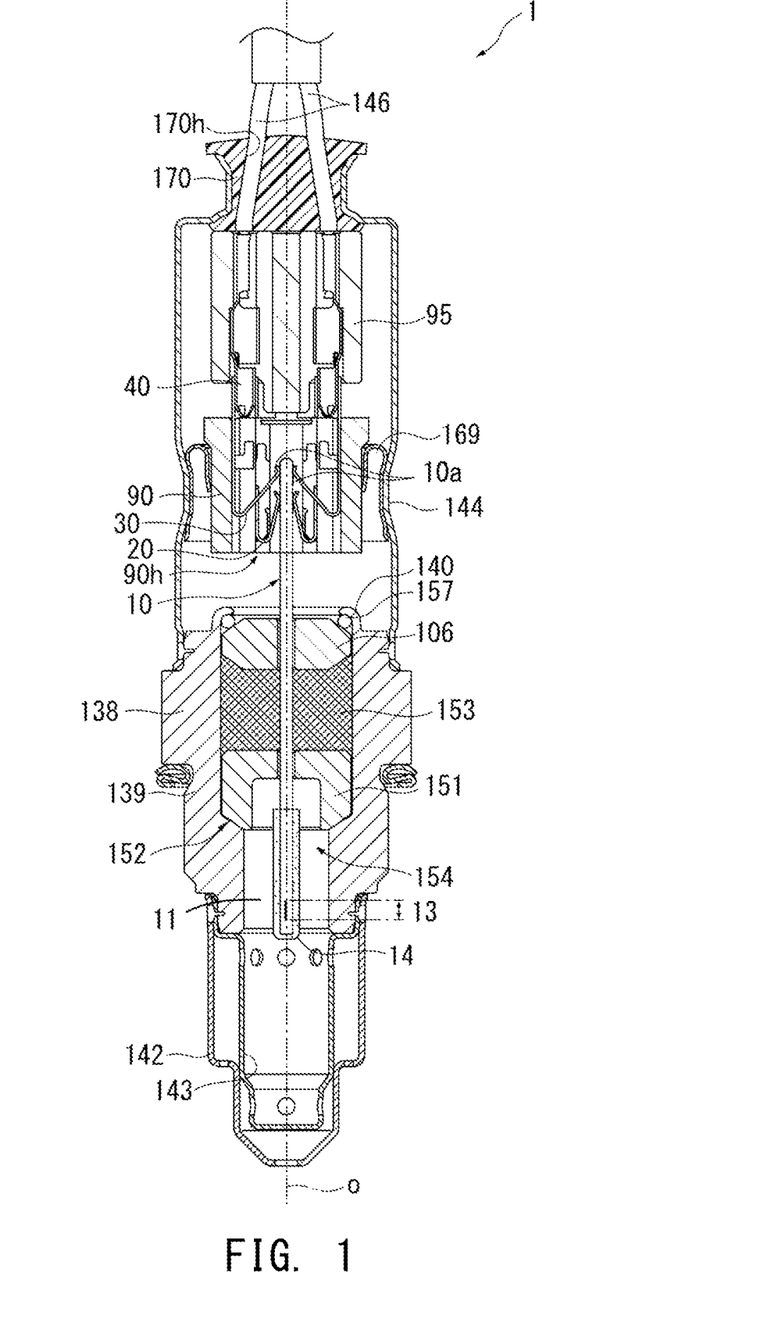
FIG. 1 is a cross-sectional view along a direction of an axial line of a gas sensor according to an embodiment of the present invention.
Figure 2:
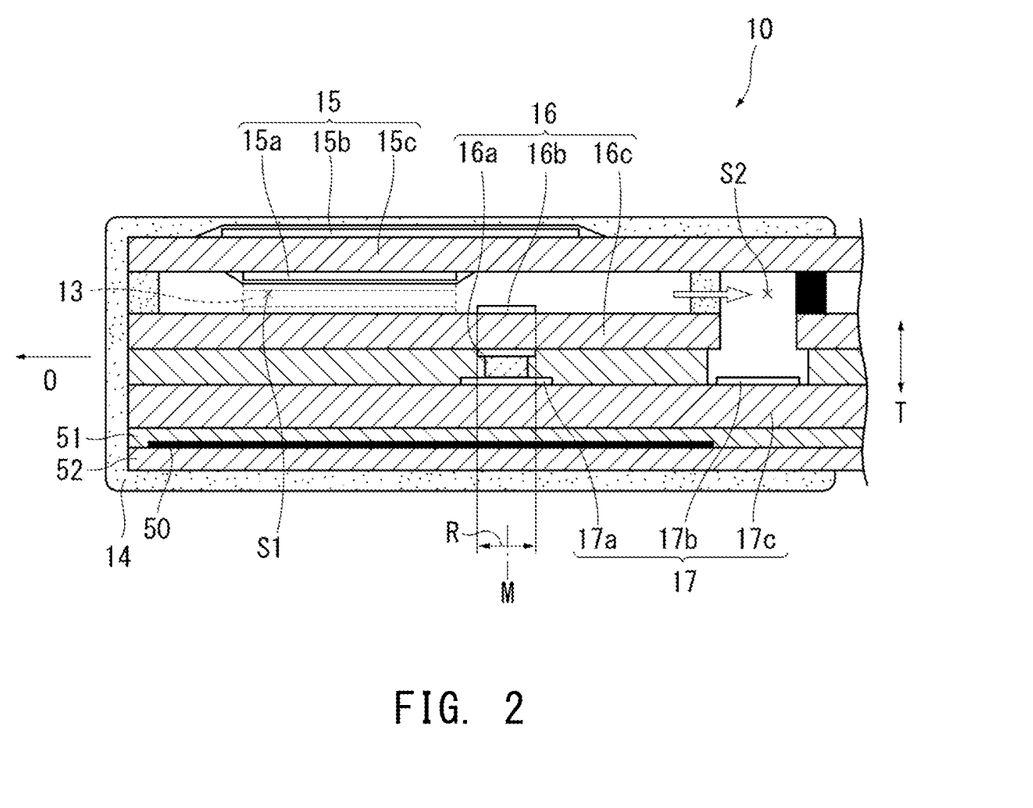
FIG. 2 is a cross-sectional view along the direction of the axial line of a sensor element.
Figure 3:
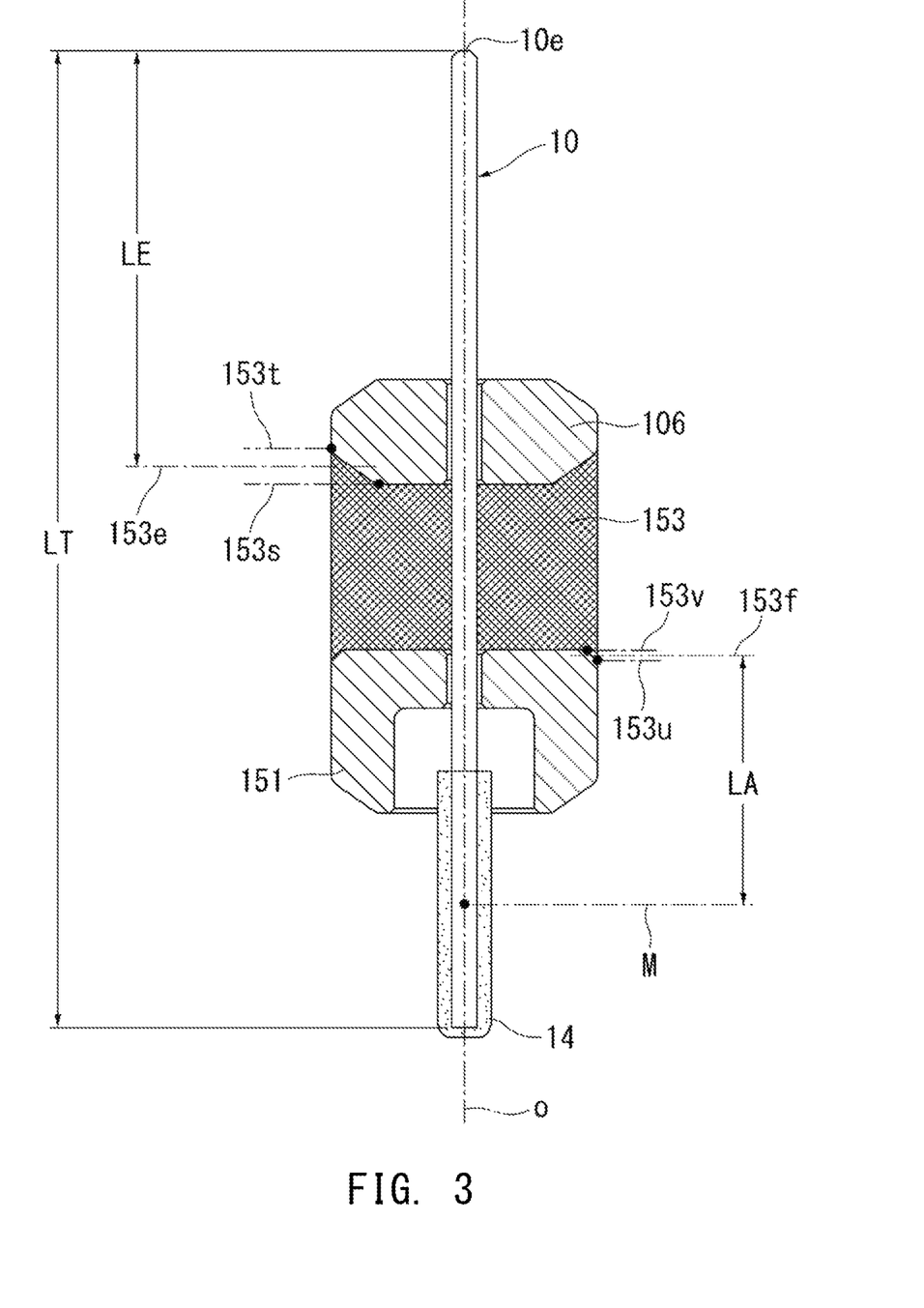
FIG. 3 is a partially enlarged view of FIG. 1.

FIG. 1 is a cross-sectional view along a direction of an axial line O of the entirety of a gas sensor (NOx sensor) 1 according to the embodiment of the present invention. FIG. 2 is a cross-sectional view along the direction of the axial line O of a sensor element 10. FIG. 3 is a partially enlarged view of FIG. 1. FIG. 1 and FIG. 3 are each a cross-sectional view along the direction of the axial line O and along a plate thickness direction T of a detection portion 11.

The gas sensor 1 is a NOx sensor for detecting the concentration of oxygen in exhaust gas from an automobile and various internal combustion engines.

In FIG. 1, the gas sensor 1 includes: a tubular metal shell 138 having an outer surface on which a screw portion 139 for fixing the gas sensor to an exhaust pipe is formed; a plate-shaped sensor element 10 extending in the direction of the axial line O (the longitudinal direction of the gas sensor 1: the up/down direction in the drawing); a tubular ceramic sleeve 106 surrounding the radial periphery of the sensor element 10; a ceramic tubular front side separator 90 disposed in an internal space on a front side of the gas sensor 1 so as to surround the periphery of a rear end portion of the sensor element 10; six front side metal terminals 20, 30 (only four of them are shown in FIG. 1) inserted and held in an insertion hole 90h penetrating the front side separator 90 in the direction of the axial line O; a ceramic tubular rear side separator 95; and six rear side metal terminals 40 (only two of them are shown in FIG. 1) held by the rear side separator 95.

The rear side separator 95 is disposed so as to contact the rear side of the front side separator 90 and is connected thereto. The front side separator 90 is held inside a sheath 144 via a holding member 169, and the rear side separator 95 contacts a grommet 170. By the elastic force of the grommet 170, the rear side separator 95 presses the front side separator 90 frontward so as to be engaged by the holding member 169.

The front side metal terminals 20, 30 oppose an outer surface of the rear side of the sensor element 10, and are electrically connected to electrode pads 10a formed on the outer surface. The rear side metal terminals 40 are joined (connected) to the rear sides of the respective front side metal terminals 20, 30. Lead wires 146 are connected to the rear sides of the respective rear side metal terminals 40.

Three electrode pads 10a are arrayed in the width direction on each of the opposed surfaces of the rear side of the sensor element 10. Each of the electrode pads 10a can be formed as a sintered body containing, for example, Pt as a main material.

On the other hand, the detection portion 11 at the front end of the sensor element 10 is coated with a porous protection layer 14 made from alumina or the like. A slit-like gas introduction portion 13 is provided in the outer surface of the sensor element 10 so as to communicate with the detection portion 11, and enables gas to flow from the outside to the detection portion 11.

The detection portion 11 will be described below.

A plate-shaped sensor element has a smaller heat capacity than a tubular sensor element, and heat from the sensor element easily escapes to the metal shell side (heat conduction). Therefore, the present invention uses a plate-shaped sensor element in which the problem of heat conduction is more pronounced.

The metal shell 138 is made from stainless steel, and is formed in a substantially tubular shape that has a through hole 154 penetrating therethrough in the direction of the axial line and that has a ledge portion 152 projecting toward the radially inner side of the through hole 154. In the through hole 154, the sensor element 10 is disposed such that a front end of the detection portion on the front side of the sensor element 10 is flush with or rearward of a front end of the through hole 154, and the detection portion faces the through hole 154.

The ledge portion 152 is formed as an inward tapered surface that is tilted with respect to a plane perpendicular to the direction of the axial line.

Inside the through hole 154 of the metal shell 138, a ceramic holder 151 having a substantially annular shape and made from alumina, a powder filled layer 153 (hereinafter, referred to also as talc ring 153), and the above-described ceramic sleeve 106 are stacked in this order from the front side to the rear side so as to surround the radial periphery of the sensor element 10 on the rear side relative to the detection portion.

The powder filled layer 153 can generally be formed from a talc powder containing, as a main component (not lower than 50 mass %), a talc (hydrous magnesium silicate $[Mg_3Si_4O_{10}(OH)_2]$) obtained by pulverizing a natural ore. As impurities, a Guangxi talc containing about 0.3 to 5 wt % of impurities composed of magnesite, etc., or a Haicheng talc containing about 1 to 30 wt % of impurities such as magnesite and dolomite, may be present, for example.

The powder filled layer 153 corresponds to the "filled member" of the invention.

A crimp packing 157 is disposed between the ceramic sleeve 106 and a rear end portion 140 of the metal shell 138. The rear end portion 140 of the metal shell 138 is crimped via the crimp packing 157 so as to press the ceramic sleeve 106 frontward.

On the other hand, as shown in FIG. 1, an outer protector 142 and an inner protector 143 which are dual protectors made from metal (for example, stainless steel) and having a plurality of hole portions, are mounted to the outer periphery on the front side (lower side in FIG. 1) of the metal shell 138 by welding or the like so as to cover a projecting portion of the sensor element 10.

The sheath 144 is fixed to the outer periphery on the rear side of the metal shell 138. The lead wires 146 are connected to the rear sides of the respective rear side metal terminals 40, and the lead wires 146 are drawn out rearward of the rear side separator 95.

At an opening portion on the rear side (upper side in FIG. 1) of the sheath 144, the grommet 170 is disposed which is made from rubber and in which lead wire insertion holes 170h are formed so as to allow the six lead wires 146 (only two of them are shown in FIG. 1) drawn out from the rear side separator 95 to be inserted therethrough.

Next, the sensor element 10 will be described with reference to FIG. 2.

The sensor element 10 includes, in the following order from the front side in the direction of the axial line O: a first pump cell 15 which pumps oxygen into or out of a detection target gas which has been introduced into a first measurement chamber S1; an oxygen concentration detection cell 16 which detects the concentration of oxygen in the first measurement chamber S1; and a second pump cell 17 in which a second pumping current flows in accordance with the concentration of NOx in a gas that has flowed into a NOx measurement chamber S2 that is in communication with the first measurement chamber S1 and which has an adjusted oxygen concentration.

The first pump cell 15 has a first solid electrolyte 15c and a pair of electrodes 15a, 15b formed on respective opposed surfaces thereof. The oxygen concentration detection cell 16 has a third solid electrolyte 16c and a pair of electrodes 16a, 16b formed on respective opposed surfaces thereof. The second pump cell 17 has a pair of electrodes 17a, 17b formed on a second solid electrolyte 17c.

All of cells 15 to 17 included in the sensor element 10 are referred to as the detection portion 11.

On the outer side (a side opposite the first pump cell 15) of the second solid electrolyte 17c, a heater 50 sandwiched between alumina insulation layers 51, 52 is stacked. The heater 50 extends in the direction of the axial line O from the front side relative to the first pump cell 15 to a position which overlaps a front end of the electrode 17b.

The heater 50 heats the cell 16 of the detection portion 11 so as to reach a set temperature.

In the present embodiment, a temperature reference position M is located on the outer surface of the sensor element 10.

A formation region R of the cell 16 is a region in which the pair of electrodes 16a, 16b overlap in the direction of the axial line O.

The temperature reference position M can be measured as follows.

(1) First, normal temperature control is performed on the sensor element 10. In this example, based on the fact that the internal impedance of the cell 16 is proportional to the temperature thereof, energization control of the heater 50 is performed such that the temperature of the cell 16 reaches the set temperature.

(2) A temperature distribution in the direction of the axial line O on the outer surface of the sensor element 10 at this time is defined as a base line, and is continuously acquired a plurality of times (30 times in this example) by means of a thermal image measurement device (thermal camera or the like).

Figure 5:
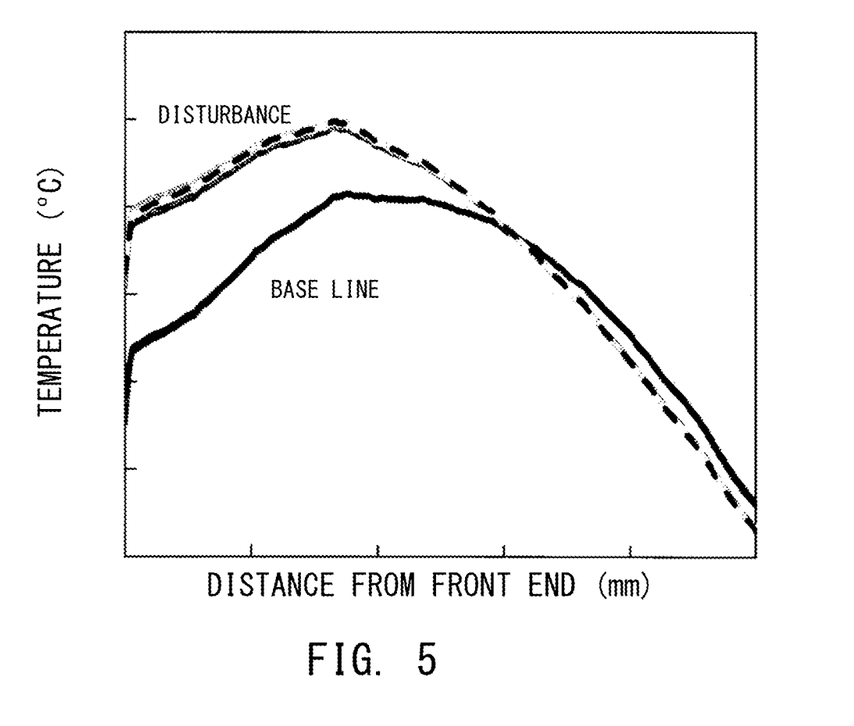
FIG. 5 is a diagram illustrating a method for measuring a temperature reference position.

(3) As a disturbance, another heat source (ceramic heater or the like) is placed close to the front end of the sensor element 10 so as to heat the front end thereof. Accordingly, the temperature gradient on the outer surface of the sensor element 10 is changed. A temperature distribution at this time is regarded as one caused by a disturbance, and is continuously acquired the same number of times (30 times) as in (2) above. FIG. 5 indicates the temperature distributions, at a base line condition and after subjecting the sensor element to a disturbance, each of which is obtained as a result of performing the measurement 30 times.

Figure 6:
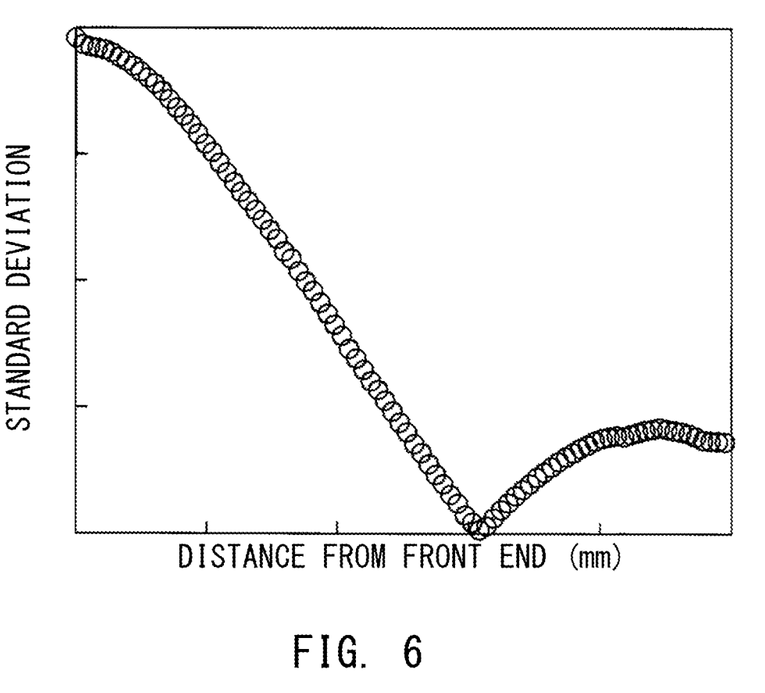
FIG. 6 is a diagram derived from the data of FIG. 5, which shows a standard deviation in temperature distribution as a function of distance from the front end.

(4) By comparing the temperature distributions obtained in (2) and (3) above, a position at which a change in temperature upon imparting a disturbance is smallest is defined as the temperature reference position M. Specifically, as shown in FIG. 6, among the temperature distribution data points obtained in (2) and (3), the data points in (2) and (3) at the same positions in the direction of the axial line O are added, and standard deviations are determined for a total of 60 data points. A position, in the direction of the axial line O, at which the deviation is smallest is defined as the temperature reference position M.

(5) The above-described measurement is performed with respect to both the direction of the axial line O and the width direction of the sensor element 10.

Here, the stacking direction of the cells 15 to 17 in FIG. 2 is the plate thickness direction T of the detection portion 11, and a direction perpendicular to the sheet of FIG. 2 is the plate width direction of the detection portion 11. A gas introduction portion 13 extending in the direction of the axial line O so as to have a shape of a slit is open in opposed side surfaces along the plate thickness direction T of the sensor element 10. The gas introduction portion 13 is disposed near the electrode 15*a* so as to be in communication with the first measurement chamber S1, and enables gas to flow from the outside through the first measurement chamber S1 to the detection portion 11.

The sensor element 10 detects the concentration of NOx as follows. First, the first pump cell 15 pumps oxygen into or out of the first measurement chamber S1 from or to the outside such that the potential difference between the electrodes of the oxygen concentration detection cell 16 becomes constant at around 425 mV.

A detection target gas having an oxygen concentration that has been adjusted in the first measurement chamber S1, is introduced into a second measurement chamber S2. In the second measurement chamber S2, NOx in the detection target gas is exposed to the electrode 17*b* of the second pump cell 17, and is decomposed (reduced) into $N_2$ and $O_2$ with the electrode 17*b* acting as a catalyst. At this time, the currents flowing in the second pump cell 17 are a current derived from NOx and a current derived from oxygen remaining in the adjusted gas that has been introduced into the second measurement chamber S2.

Here, the concentration of oxygen which remains in the first measurement chamber S1 after pumping is adjusted to a predetermined value as described above. Therefore, the current derived from the remaining oxygen can be regarded as being substantially constant, and has a small influence on variation in the current derived from NOx. Thus, the current flowing in the second pump cell 17 is proportional to the concentration of the NOx.

Next, a characteristic part of the present invention will be described with reference to FIG. 3.

As shown in FIG. 3, as viewed in the direction of the axial line O, an overall length LT of the sensor element 10 is not larger than 50 mm, a length LE from a rear end 153*e* of the powder filled layer 153 to a rear end 10*e* of the sensor element 10 is not smaller than 13.5 mm, and a length LA from the temperature reference position M to a front end 153*f* of the powder filled layer 153 is larger than 5.0 mm and not larger than 11.5 mm.

Here, the overall length LT is a length excluding the length of the porous protection layer 14.

As shown in FIG. 3, a rear side of the powder filled layer 153 that is in contact with the ceramic sleeve 106 is tapered so as to become narrower from a rearmost end 153*t* toward a front end portion 153*s*. Here, an intermediate point in the direction of the axial line O between the rearmost end 153*t* and the front end portion 153*s* is defined as the rear end 153*e*. Similarly, a front side, of the powder filled layer 153 that is in contact with the ceramic holder 151 is tapered so as to become narrower from a frontmost end 153*u* toward a rear end portion 153*v*. Here, an intermediate point in the direction of the axial line O between the frontmost end 153*u* and the rear end portion 153*v* is defined as the front end 153*f*.

If LT is larger than 50 mm, the length of the sensor element 10 becomes large and it becomes difficult to reduce the size of the gas sensor 1.

If LE is smaller than 13.5 mm, the dimension of the electrode pad 10*a* and the interval between the electrode pads 10*a* are excessively shortened, and thus, the reliability of electrical connection with the metal terminals 20, 30 may be reduced, or short-circuiting may occur.

Even if LE is set to not smaller than 13.5 mm, the reliability of electrical connection with the metal terminals 20, 30 may be reduced if the thickness in the direction of the axial line O of a support member (ceramic sleeve 106 in FIG. 3) supporting the rear side of the powder filled layer 153 is excessively large. Thus, a maximum thickness ts of the above-described support member is preferably set to not larger than 5.5 mm. In a case where a plurality of the above-described support members are stacked in the direction of the axial line O, the maximum thickness of the laminate thereof is defined as ts.

Figure 4:
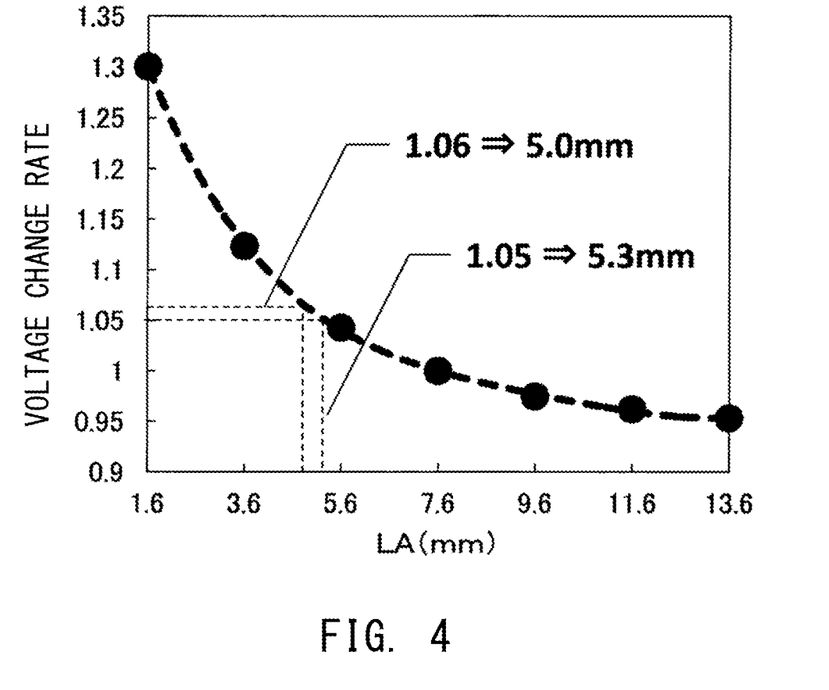
FIG. 4 is a diagram indicating the change rate of energization voltage of a heater with a change in the length LA.

FIG. 4 indicates the change rate of energization (heating) voltage of the heater 50 with a change in LA, in an example described below. As understood from FIG. 4, when LA does not exceed 5.0 mm, a voltage change rate relative to a specified value for the energization voltage becomes higher than 5%. Consequently, the power to be supplied to the heater 50 increases, and it becomes difficult to heat the gas sensor element to an operating temperature at a low voltage.

On the other hand, if LA exceeds 11.5 mm, there is no choice but to adjust the length in the direction of the axial line O of the powder filled layer 153 so as to correspondingly shorten the length in order to reduce the size of the gas sensor 1. In this case, the sealability of the gap between the metal shell 138 and the sensor element 10 is reduced.

As described above, by setting LT to not larger than 50 mm, the size of the gas sensor 1 can be reduced. In addition, by setting LA within a range greater than 5.0 mm and not greater than 11.5 mm, there is a small variation in heat conduction from the sensor element 10 to the powder filled layer 153. This is the case even if there is a variation in LA at the time of gas sensor assembly, whereby an increase in power to be supplied to the heater 50 can be suppressed. As a result, the gas sensor element can be operated at a low voltage.

If LA is not smaller than 6.7 mm and not greater than 10.7 mm, the change in rate of the energization (heating) voltage of the heater 50 becomes not higher than 3%, whereby an increase in power to be supplied to the heater 50 can be further suppressed.

The present invention is not limited to the above-described embodiment, but is applicable to various modifications and equivalents encompassed by the claims appended hereto.

For example, the temperature reference position M may be located in the formation region R of the cell 16. That is, based on the fact that the internal impedance of a cell is proportional to the temperature thereof, the position of a specific cell is defined as the temperature reference position M. Energization control of the heater 50 is performed such that the temperature of the cell reaches the set temperature. On the other hand, when a certain temperature reference position M is determined in advance, the electric resistance of the heater 50 at this position may be monitored. Based on the fact that the electric resistance is proportional to temperature, energization control of the heater 50 may be performed such that the temperature reaches the set temperature. Alternatively, the temperature reference position M may be located in a formation region not on the cell 16 but on the cell 17.

Figure 7:
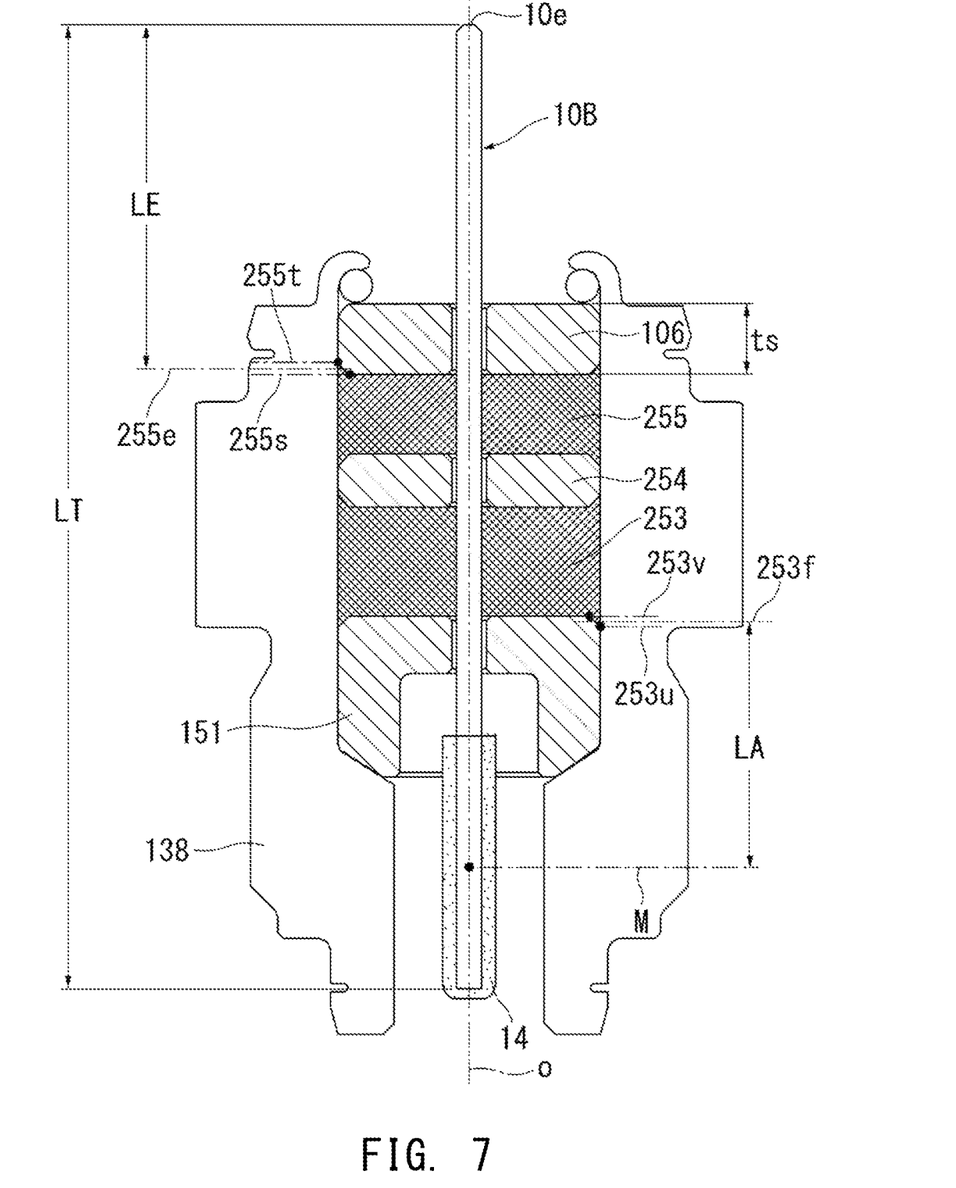
FIG. 7 is a cross-sectional view along the direction of the axial line of a sensor element of a gas sensor including a plurality of filled members.

As shown in FIG. 7, a sensor element 10B may include a plurality of filled members 253, 255 in the direction of the axial line O. The sensor element 10B shown in FIG. 7 has a metal shell 138 in which the same ceramic holder 151 as that in FIG. 1, the first filled member 253, a tubular ceramic ring 254, the second filled member 255, and the same ceramic sleeve 106 as that in FIG. 1 are stacked in this order from the front side to the rear side.

Similarly to the sensor element 10 in FIG. 1, the first filled member 253 and the second filled member 255 are powder filled layers (talc rings) filled between the inner peripheral surface of the metal shell 138 and the outer peripheral surface of the sensor element 10B so as to seal the gap between the metal shell 138 and the sensor element 10B.

In order to insert the sensor element 10B, small gaps are formed between the sensor element 10B and each of the ceramic holder 151, the ceramic ring 254, and the ceramic sleeve 106. Heat conduction from the sensor element 10B occurs mainly between the sensor element 10B and the filled members 253, 255.

Here, between the filled members 253, 255, heat conduction from the sensor element 10B is more conspicuous at the first filled member 253 positioned so as to be closer to a front end of the sensor element 10B, and the first filled member 253 has a greater influence on an increase, due to the heat conduction, in power to be supplied to the heater.

Thus, the above-described LA is defined with respect to the first filled member 253, whereby, even in the case where the sensor element 10B includes a plurality of filled members 253, 255, an increase in power to be supplied to the heater can be suppressed, and the gas sensor element can also be operated at a low voltage.

Specifically, the length in the direction of the axial line O from the temperature reference position M to a front end 253*f* of the first filled member 253 is defined as LA.

Similarly to the powder filled layer 153 in FIG. 3, in a case where a front side of the filled member 253 is tapered so as to become narrower from a frontmost end 253*u* toward a rear end portion 253*v*, an intermediate point in the direction of the axial line O between the frontmost end 253*u* and the rear end portion 253*v* is defined as the front end 253*f*.

Furthermore, between the filled members 253, 255, the above-described LE is defined with respect to the second filled member 255 positioned so as to be farther from the sensor element 10B. Consequently, even in the case where the sensor element 10B includes a plurality of filled members 253, 255, the reliability of electrical connection with the metal terminals and the like can be improved.

Specifically, the length in the direction of the axial line O from a rear end 255*e* of the second filled member 255 to the rear end 10*e* of the sensor element 10B is defined as LE.

Similarly to the powder filled layer 153 in FIG. 3, in a case where a rear side of the second filled member 255 is tapered so as to become narrower from a rearmost end 255*t* toward a front end portion 255*s*, an intermediate point in the direction of the axial line O between the rearmost end 255*t* and the front end portion 255*s* is defined as the rear end 255*e*.

The same applies to a case where three or more filled members are provided in the direction of the axial line of the sensor element. LA may be defined with respect to a filled member that is closest to the front end of the sensor element 10B, and LE may be defined with respect to a filled member that is farthest from the sensor element 10B.

In addition to a NOx sensor, examples of the gas sensor to which the present invention may be applied include an oxygen sensor and a full range gas sensor.

Instead of a powder filled member filled with talc, glass or the like may be used to fill the filled member.

Example

Gas sensors 1 shown in FIG. 1 were manufactured, with LT being 38 mm, LE being not smaller than 13.5 mm, and LA being variously changed. The temperature reference position M was obtained as in the above-described method. For each of the gas sensors 1, the maximum value of energization voltage of the heater 50 at the time of normal temperature control was measured, and the voltage change rate of the energization voltage was obtained with the energization voltage of the heater 50 of a reference sensor (LA=7.7 mm) being defined as 1.

The results thus obtained are shown in FIG. 4.

When LA exceeded 5.0 mm, the voltage change rate was not higher than 5%. When LA was not smaller than 6.7 mm and not greater than 10.7 mm, the voltage change rate was not higher than 3%.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2017-140713 filed Jul. 20, 2017, the disclosure of which is incorporated herein by reference in its entirety.

What is claimed is:

1. A gas sensor comprising:
a sensor element which is plate-shaped so as to extend in a direction of an axial line and which includes a detection portion arranged at a front side of the sensor element having at least one cell comprising a solid electrolyte and a pair of electrodes formed on the solid electrolyte and which includes a heater configured to heat the detection portion, the sensor element having a front end and a rear end;
a metal shell which has a through hole penetrating therethrough in the direction of the axial line and which surrounds a periphery of the sensor element; and
a filled member filled with a filling material between an inner side surface of the metal shell and an outer surface of the sensor element so as to seal a gap between the metal shell and the sensor element, the filled member having a front end and a rear end,
the sensor element being configured to be heated to a set temperature by the heater, wherein
a position at which a resulting change in temperature of the sensor element is smallest when a disturbance is applied thereto is defined as a temperature reference position,
the filled member is positioned rearward of the temperature reference position of the sensor element,
an overall length LT in the direction of the axial line of the sensor element is not greater than 50 mm,
a length LE in the direction of the axial line from the rear end of the filled member to the rear end of the sensor element is not smaller than 13.5 mm, a length LA in the direction of the axial line from the temperature reference position to a front end of the filled member is greater than 5.0 mm and not greater than 11.5 mm, and the temperature reference position is a position of a region in which electrodes constituting a detection cell configured to detect a specific gas component in a measurement target gas overlap.

2. The gas sensor as claimed in claim 1, wherein LA is not smaller than 6.7 mm and not greater than 10.7 mm.

3. The gas sensor as claimed in claim 1, wherein the filled member is filled with talc.

4. The gas sensor as claimed in claim 1, wherein the filled member includes a first filled member and a second filled member arranged on a rear side of the first filled member, a length in the direction of the axial line from a rear end of the second filled member positioned so as to be farthest from the sensor element, to the rear end of the sensor element, is defined as LE, and a length in the direction of the axial line from the temperature reference position to a front end of the first filled member positioned so as to be closest to a front end of the sensor element is defined as LA.

* * * * *